(12) United States Patent
Amemiya et al.

(10) Patent No.: US 11,436,723 B2
(45) Date of Patent: Sep. 6, 2022

(54) IMAGE DIAGNOSIS SUPPORT DEVICE, IMAGE DIAGNOSIS SUPPORT PROGRAM, AND MEDICAL IMAGE ACQUISITION APPARATUS

(71) Applicant: Hitachi, Ltd., Tokyo (JP)

(72) Inventors: Tomoki Amemiya, Tokyo (JP); Ryota Satoh, Tokyo (JP); Suguru Yokosawa, Tokyo (JP); Toru Shirai, Tokyo (JP); Hisaaki Ochi, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 281 days.

(21) Appl. No.: 16/879,812

(22) Filed: May 21, 2020

(65) Prior Publication Data

US 2020/0380676 A1 Dec. 3, 2020

(30) Foreign Application Priority Data

May 28, 2019 (JP) .............................. JP2019-099173

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0042* (2013.01); *A61B 5/0263* (2013.01); *A61B 5/055* (2013.01); *A61B 5/4842* (2013.01); *A61B 5/7257* (2013.01); *A61B 5/7264* (2013.01); *A61B 8/06* (2013.01); *G06T 2207/10088* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

2005/0043614 A1* 2/2005 Huizenga ............... A61B 5/055
600/427
2018/0140219 A1* 5/2018 Yin ........................ G16H 40/67
(Continued)

FOREIGN PATENT DOCUMENTS

JP 2006-043007 A 2/2006

*Primary Examiner* — Idowu O Osifade
(74) *Attorney, Agent, or Firm* — Mattingly & Malur, PC

(57) ABSTRACT

Provided is a technique for supporting a diagnosis in determining disease by using various types of measured values acquired by a medical image acquisition apparatus. An image diagnosis support device includes a measured-value receiving unit configured to receive various types of measured values at a plurality of positions within a living body, a group generator configured to generate groups of the measured values depending on the position or the type of the measured value, an intermediate index calculator configured to calculate an intermediate index from the measured values included in the group on a per-group basis, and a comprehensive index calculator configured to calculate a comprehensive index from values of the intermediate index calculated on a per-group basis. The intermediate index and the comprehensive index are displayed on a display unit in a display mode such as numerical values and in the form of an image.

13 Claims, 13 Drawing Sheets

(51) Int. Cl.
*A61B 8/06* (2006.01)
*A61B 5/055* (2006.01)
*A61B 5/026* (2006.01)

(56) References Cited

U.S. PATENT DOCUMENTS

2020/0126231 A1* 4/2020 Hu .................. A61B 6/5247
2020/0203004 A1* 6/2020 Shanbhag .............. G16H 50/20
2020/0261032 A1* 8/2020 Li ..................... G01T 1/2023

* cited by examiner

FIG. 12

| | REGION A | REGION B | REGION C | REGION D | |
|---|---|---|---|---|---|
| MEASURED VALUE 1 | p11 | p21 | p31 | p41 | p1 |
| MEASURED VALUE 2 | p12 | p22 | p32 | p42 | p2 |
| MEASURED VALUE 3 | p13 | p23 | p33 | p43 | p3 |
| MEASURED VALUE 4 | p14 | p24 | p34 | p44 | p4 |
| MEASURED VALUE 5 | p15 | p25 | p35 | p45 | p5 |

⎧ p1 p2 p3 p4 p5 ⎫ P

▢ FIRST GROUP
▢ SECOND GROUP

IMAGE DIAGNOSIS SUPPORT DEVICE, IMAGE DIAGNOSIS SUPPORT PROGRAM, AND MEDICAL IMAGE ACQUISITION APPARATUS

INCORPORATION BY REFERENCE

The present application claims priority from Japanese patent application JP-2019-99173 filed on May 28, 2019, the content of which is hereby incorporated by reference into this application.

BACKGROUND OF THE INVENTION

Field of the Invention

The present invention relates to an image diagnosis support technique for supporting image diagnosis, by using measured data obtained by a medical image acquisition apparatus.

Description of the Related Art

As a medical image acquisition apparatus for non-invasively obtaining an image such as a tomographic image representing a human body anatomically, there are widely used imaging apparatuses including a magnetic resonance imaging (MRI) apparatus, a CT (Computed Tomography) apparatus, and an ultrasonic diagnostic apparatus. In those apparatuses, computations are applied to measured data being acquired, and an obtained image is displayed in the form of diagnostic image on its accompanying display unit or on an independent display unit.

By way of example, the MRI apparatus is capable of taking an image of any cross section of a subject by utilizing a nuclear magnetic resonance phenomenon, mainly of proton, allowing acquisition of not only morphological information but also information related to living-body functions such as bloodstream and metabolic functions. In the MRI apparatus, generally, there is acquired a weighted image where a relative difference in physical property values is enhanced, the values being related to nuclear magnetic resonance in a living body tissue, for example, longitudinal relaxation time (T1), transverse relaxation time (T2), and proton density (PD). Further in the MRI apparatus, there is also acquired an image of calculated values, which is created from values such as a diffusion coefficient according to computations between images.

In the CT apparatus, a quantitative image where CT values are visualized can be obtained, and in the ultrasonic diagnostic apparatus, a quantitative image where a reflectivity and a flow velocity are visualized can be obtained. Further according to the ultrasonic diagnostic apparatus, there are also obtained a Doppler image including blood flow information, in addition to a B-mode image being a morphological image.

The weighted image and the quantitative image as described above may be different in physical quantities, respectively, representing degrees of enhancement in living body tissue and representing pixel values. Therefore, it is now a common practice to take various types of images for diagnosis, so as to perform comprehensive diagnosis.

In conventional diagnosis, a user, i.e., a doctor, visually checks those images to determine abnormalities or a type of disease. As a method for automating such procedures to support diagnosis, there is disclosed in Japanese Unexamined Patent Application Publication No. 2006-043007 (hereinafter, referred to as Patent Literature 1), a method for calculating a feature of a region of interest (ROI) in an image, and displaying an index for diagnosis, such as the degree of malignancy, with the use of neural network.

As described above, there are many various types of images that can be measured by the medical image acquisition apparatuses. In some cases, a comprehensive judgment becomes necessary, with checking measured values of multiple areas in various types of images, for example, for the case of diagnosing as dementia (major neurocognitive disorder), using data such as atrophy of the hippocampus and temporal lobe, and reduction of cerebral blood flow in the occipital lobe. For determining disease using more than one area in various types of images for diagnosis, it is considered to utilize a method for supporting this type of diagnosis, as described in the Patent Literature 1. That is, according to this method, features of respective ROIs in a large number of images are calculated, and indexes for diagnosis such as the degree of malignancy are displayed, with the use of machine learning including a neural network. According to this method, however, there is a problem that as the number of image types is increased, the volume of features is also increased. Therefore, when there is less data used for learning, machine learning becomes less accurate. Furthermore, Patent Literature 1 discloses that a contribution ratio to a diagnosis result is displayed as to a part of or all of entered features. However, if there are a large number of features being entered, this causes a problem that it is difficult for a user to grasp all the features, impairing determination with certainty.

The present invention has been made in view of the situation as discussed above, and an object of the present invention is to provide a technique for supporting a diagnosis when determining disease by using various types of measured values (e.g., images) acquired by the medical image acquisition apparatus, allowing highly accurate determination and easy identification of the basis of the determination.

SUMMARY OF THE INVENTION

In order to solve the problems as described above, the present invention divides a plurality of measured values acquired by a medical image acquisition apparatus, into a plurality of groups depending on an attribute of the measured value, calculates an intermediate index as a diagnosis index by using the measured values on a per-group basis, and then merges values of the intermediate index of the groups to obtain a comprehensive index.

In other words, an image diagnosis support device of the present invention includes a measured-value receiving unit configured to receive various types of measured values at a plurality of positions within a living body, a group generator configured to generate a plurality of measured-value groups depending on the position or the type, an intermediate index calculator configured to calculate an intermediate index from the measured values included in the group on a per-group basis, and a comprehensive index calculator configured to calculate a comprehensive index from the values of the intermediate index calculated on a per-group basis.

A medical image acquisition apparatus of the present invention includes a measurement unit configured to acquire various types of measured values at a plurality of positions in a subject, and a computing unit configured to perform computations using the various types of measured values acquired by the measurement unit, wherein the computing unit includes a group generator configured to divide the various types of measured values into a plurality of groups, an intermediate index calculator configured to calculate an intermediate index from the measured values included in the group on a per-group basis, and a comprehensive index calculator configured to calculate a comprehensive index from values of the intermediate index calculated on a per-group basis. The intermediate index and the comprehensive index are displayed in predetermined forms, for example, on a display unit.

According to the present invention, in determining disease with the use of the various types of images acquired by the medical image acquisition apparatus, accuracy in determination is enhanced, and identification of the basis of the determination is facilitated.

BRIEF DESCRIPTION OF THE DRAWINGS

FIG. 12 illustrates one example of the groups generated by the group generator according to the second embodiment.

DETAILED DESCRIPTION OF THE PREFERRED EMBODIMENTS

Figure 1:
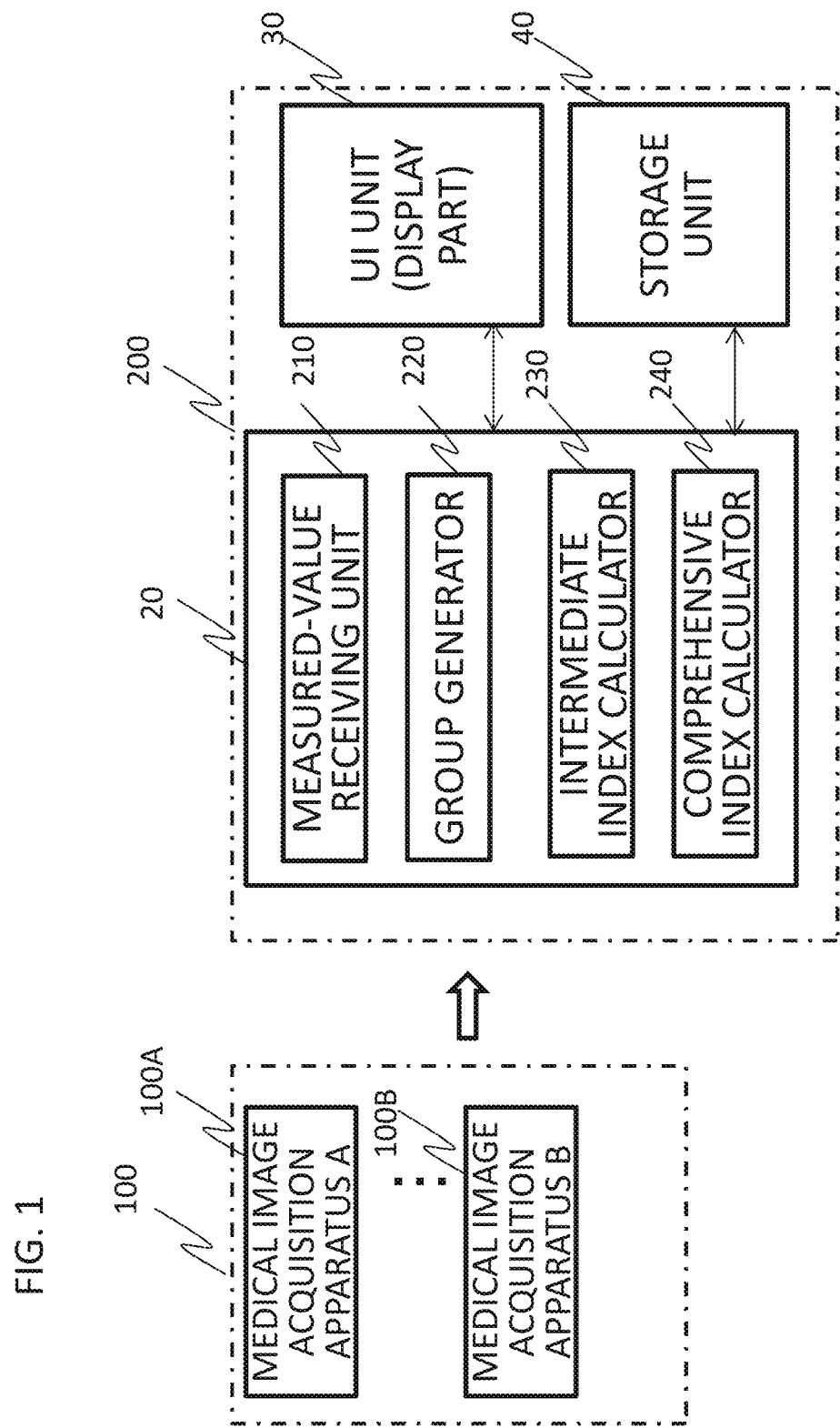
FIG. 1 is a block diagram showing one embodiment of an image diagnosis support device.

There will now be described embodiments of a medical image acquisition apparatus and an image diagnosis support device according to the present invention, with reference to the accompanying drawings. It is to be noted the scope of the present invention will not be restricted by the descriptions below. In all the figures illustrating the embodiments of the present invention, elements with an identical function are labeled with the same reference numeral, unless otherwise specified, and they will not be redundantly described.

Hereinafter, an embodiment of the image diagnosis support device will be described. The image diagnosis support device may be independent of the medical image acquisition apparatus, such as an MRI apparatus, a CT apparatus, and an ultrasonic imaging apparatus, or the image diagnosis support device may be incorporated in the medical image acquisition apparatus. In the latter case, functions of the image diagnosis support device may be implemented mainly by a computer provided in the medical image acquisition apparatus.

As shown in FIG. 1, the image diagnosis support device 200 of the present embodiment is provided with a computer (image diagnosis support unit) 20 configured to receive measured data from the medical image acquisition apparatus 100 and to perform image diagnosis support processing, and a user interface (UI) unit 30 configured to display an image acquired by the medical image acquisition apparatus 100 and a computation result from the computer 20, and to receive a command from a user. The computer 20 may be accompanied with a storage unit 40 configured to store the measured data, computation results, data necessary for the computation, and others.

Measured values received by the image diagnosis support device 200 may come from one medical image acquisition apparatus 100, or from a plurality of medical image acquisition apparatuses 100A, 100B, and so on. The medical image acquisition apparatus 100 may be an MRI apparatus, a CT apparatus, and an ultrasonic imaging apparatus, for instance.

The computer 20 includes a CPU and a memory, and it is further provided with a measured-value receiving unit 210 configured to receive various types of measured values at a plurality of positions from the medical image acquisition apparatus 100, a group generator 220 configured to divide the various types of measured values into groups, depending on attributes, for example, depending on body parts (regions) and types of the measured values (whether the value is a pixel value or a physical property value of a reconstructed image, what kind of physical property value it is, and so on), an intermediate index calculator 230 configured to calculate an intermediate index as a diagnostic index, by using the measured values included in each group on a per-group basis, and a comprehensive index calculator 240 configured to calculate a comprehensive index as a comprehensive diagnostic index, by using values of the intermediate index calculated by the intermediate index calculator 230.

The CPU reads programs stored in advance in the memory and executes those programs, thereby allowing software to implement functions of those units as described above. The computer 20 of the present embodiment is not limited to the configuration that implements the functions by software, but the computer may be configured such that all or a part of the functions are implemented by hardware such as custom IC like ASIC (Application Specific Integrated Circuit) and programmable IC like FPGA (Field Programmable Gate Array). The storage unit 40 holds various data necessary for the processing in the computer 20.

Indexes calculated by the intermediate index calculator 230 and the comprehensive index calculator 240 may include, for example, an index indicating whether a subject is in normal condition or not, an index indicating whether the subject contracts a certain disease or not and the degree of the disease progression, or an index indicating which disease out of multiple diseases (which disease has the highest probability). The intermediate index may represent the same index as the comprehensive index, or they represent different indexes. A specific method for calculating the indexes will be described in detail in the following embodiment.

The UI unit 30 displays the measured values received by the measured-value receiving unit 210 and the indexes calculated by the computer 20 (the intermediate index and the comprehensive index). In addition, the UI unit 30 receives entries of conditions to perform imaging, and an instruction from the user for creating an image and calculating the indexes.

Figure 2:
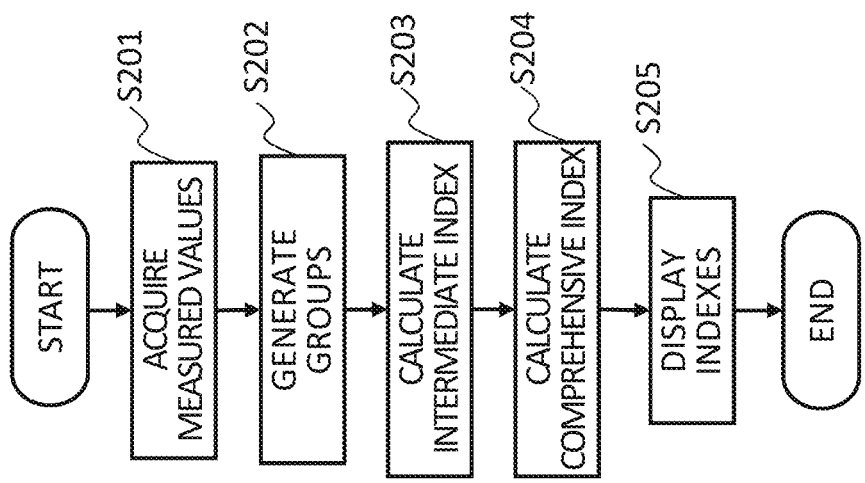
FIG. 2 is a flowchart showing an operation of the image diagnosis support device as shown in FIG. 1.

With reference to FIG. 2, an operation of the image diagnosis support device 200 (processing procedures of the computer) according to the present embodiment will be described.

The measured-value receiving unit 210 captures a plurality of measured values directly from the medical image acquisition apparatus 100, or from the storage unit 40, in response to diagnostic details such as a disease to be determined, which is specified via the UI unit 30 (S201). The measured values may correspond to an image (original image) itself acquired by the medical image acquisition apparatus 100, or the measured values may be predetermined quantitative values calculated from the original image, a quantitative image having the quantitative values as pixel values, or a certain statistics calculated from the original image or the quantitative image.

Next, the group generator 220 divides thus captured multiple measured values into groups (S202). Grouping is performed on the basis of an attribute of the measured value. For example, a plurality of measured values is put into one group on a region-by-region basis, or the measured values in a plurality of regions are put into one group on a measured-value type basis. In this situation, the number of the measured values constituting the group may be the same across the groups, or it may be different group by group. All the measured values may belong to any of the groups, or some of the measured values may not be used for the following index calculation.

A rule for the grouping, on a region-by-region basis or on a measured-value type basis, may be determined in advance. Alternatively, the rule may be determined depending on a target for diagnosis. The rule may be provided by the user via a user interface screen prepared for the image diagnosis support.

Next, the intermediate index calculator 230 uses the measured values in each group to calculate the intermediate index (S203). For calculating the index, a publicly-known machine learning algorithm or neural network may be employed. In other words, a function with a coefficient decided according to the relation between measured values and an evaluation result (index) having been obtained from another subject that is different from a test subject, or a trained neural network, are used to calculate the intermediate index of the measured values of the group. A machine learning algorithm used for the calculation is selected as appropriate depending on the index to be calculated.

Finally, the comprehensive index calculator 240 merges values of the intermediate index in the respective groups to calculate a comprehensive index (S204). Calculation of the comprehensive index may be weighted-addition of the values of the intermediate index, for example, or it is calculated according to the machine learning algorithm or the neural network, using the relation between the intermediate index and the comprehensive index. As described above, the index may indicate the presence or absence of abnormality, the probability of a certain disease, a degree of disease progression, and so on.

The image diagnosis support device 200 displays thus calculated intermediate index and comprehensive index on the UI unit 30 (S205).

There are various modes for displaying these indexes, and the intermediate index and the comprehensive index may be displayed in the form of numerical values or codes, or an image having pixel values of numerical values obtained on a pixel-by-pixel basis.

According to the image diagnosis support device of the present embodiment, when a disease is determined and diagnosed on the basis of a plurality of measured values, the measured values are divided into groups depending on the attributes of the measured values, then a diagnostic index is calculated on a per-group basis, and those diagnostic index values are merged to present a final diagnostic index. Thus, an accurate result can be obtained without a necessity of a large number of learning data for calculating the intermediate index. In addition, since the intermediate index values are presented group by group, a basis for calculating the comprehensive index can be identified easily, along with enabling verification of the basis, for example, indicating what kind of measured values for what kind of regions have been used to calculate the comprehensive index. In addition, grouping on a region-by-region basis may facilitate identification of the region that includes abnormality.

Next, embodiments of specific processing performed in the image diagnosis support device will be described, taking an example where an MRI apparatus serves as the medical image acquisition apparatus.

First Embodiment

First, a configuration of the MRI apparatus and measured values acquired by the MRI apparatus will be described.
[Configuration of the Apparatus]

Figure 3:
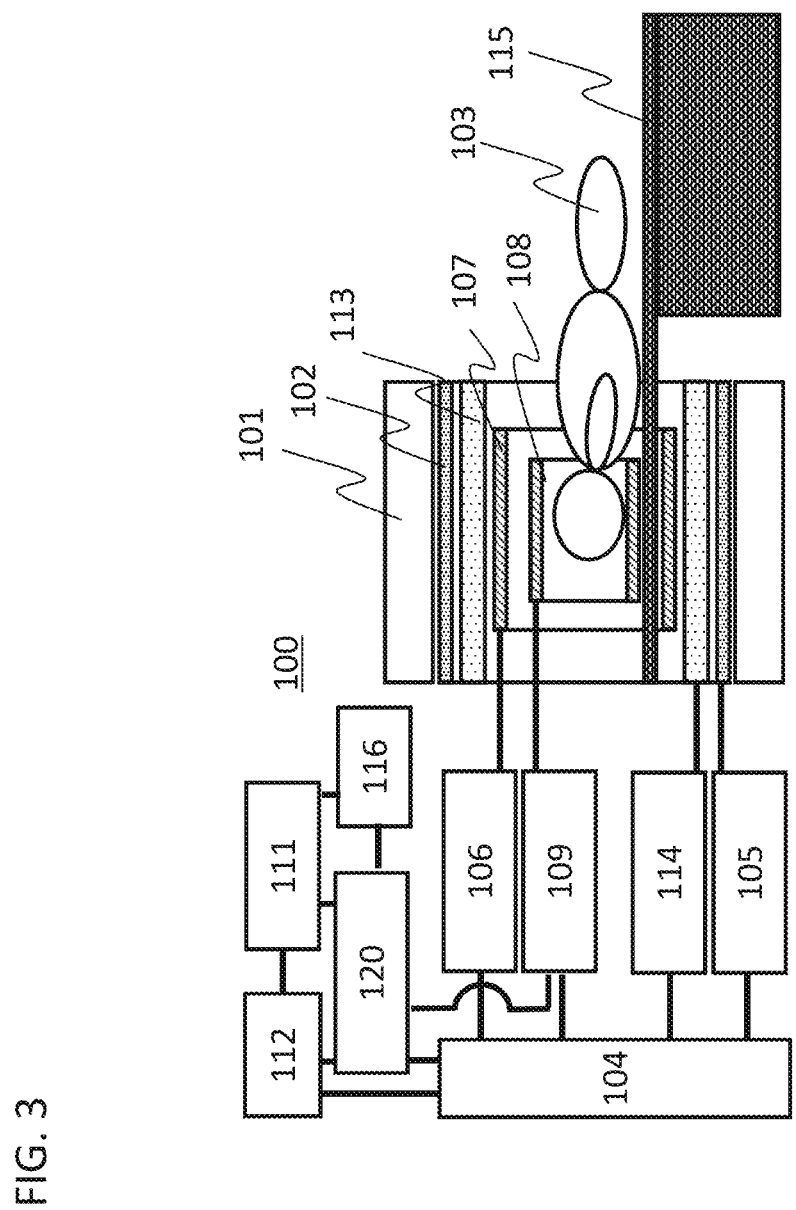
FIG. 3 is a block diagram showing a typical configuration of a medical image acquisition apparatus (MRI apparatus) according to a first embodiment.

Main configuration of the MRI apparatus 100 is the same as a publicly known MRI apparatus, and as shown in FIG. 3, the MRI apparatus 100 is provided with a magnet 101 for generating a static magnetic field, a gradient coil 102 for generating a gradient magnetic field, an RF coil 107 for applying pulses to a subject (e.g., a living body) 103, an RF probe 108 for detecting echo signals generated from the subject 103, and a table 115 for placing the subject 103 within the space of the static magnetic field generated from the magnet 101.

The MRI apparatus 100 is further provided with a gradient power supply 105 for driving the gradient coil 102, an RF magnetic field generator 106 for driving the RF coil 107, a receiver 109 for performing detection of the echo signals detected by the RF probe 108, and a sequencer 104. The sequencer 104 sends commands to the gradient power supply 105 and to the RF magnetic field generator 106, allowing generation of the gradient magnetic field and the RF magnetic field, respectively. Then, the sequencer provides a receiver 109 with nuclear magnetic resonance frequency, being a reference for the detection. Those units in the MRI apparatus 100 as described so far are collectively referred to as a measurement unit 110.

The MRI apparatus 100 is further provided with a computer 120 for performing signal processing on the signals having undergone detection in the receiver 109, a display unit 111 for displaying a result of the processing performed by the computer 120, a storage unit 112 for holding a result of the processing, and an input unit 116 for receiving an instruction from the user. The display unit 111 is arranged in proximity to the input unit 116, and those units function as a user interface unit.

Figure 4:
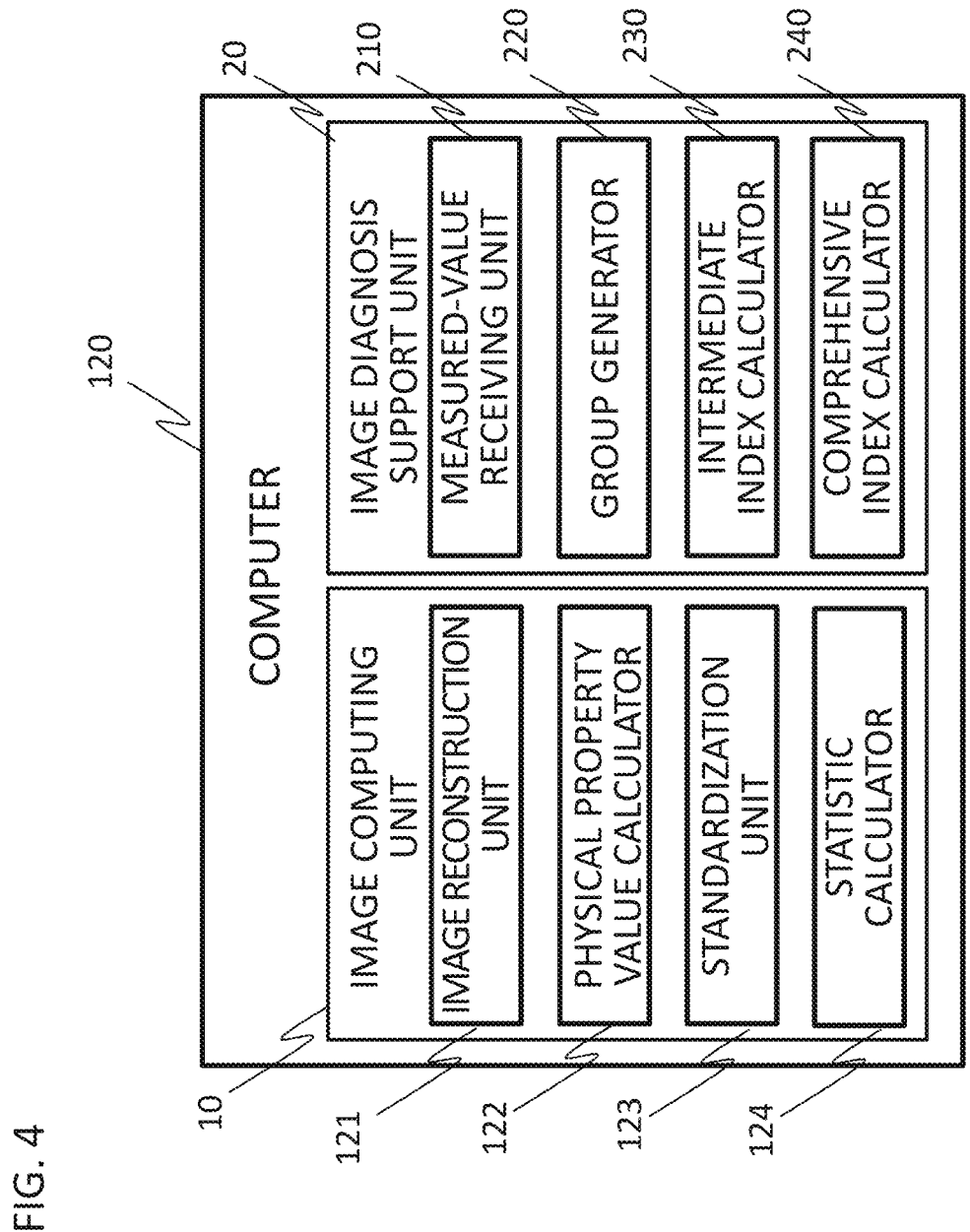
FIG. 4 is a block diagram showing a configuration of a computer according to the first embodiment.

The computer 120 includes a CPU and a memory, and executes computational functions such as image reconstruction (computing unit), and control functions for controlling elements constituting the operations of the measurement unit 110 (controller). In addition, the MRI apparatus may be provided with the image diagnosis support function. FIG. 4 illustrates a configuration example of the computer 120 in the MRI apparatus provided with the image diagnosis support function. As shown in FIG. 4, the computing unit of the computer 120 incorporates an image computing unit 10 and an image diagnosis support unit 20. The image computing unit 10 is provided with an image reconstruction unit 121, and when necessary, further provided with a physical property value calculator 122, a standardization unit 123, and a statistic calculator 124. The configuration of the image diagnosis support unit 20 is the same as the configuration of the computer in the image diagnosis support device 200 as shown in FIG. 1, and it is provided with the measured-value receiving unit 210, the group generator 220, the intermediate index calculator 230, and the comprehensive index calculator 240.

The CPU reads programs stored in advance in the memory and executes those programs, thereby allowing software to implement those function of the computer 120. The computer 120 of the present embodiment is not limited to the configuration that implements the functions by software, but the computer may be configured such that all or a part of the functions are implemented by hardware such as custom IC like ASIC (Application Specific Integrated Circuit) and programmable IC like FPGA (Field Programmable Gate Array).

The MRI apparatus 100 may also be provided with a shim coil 113 and a shim power supply 114 for driving the shim coil 113, when controlling of static magnetic field homogeneity is necessary. The shim coil 113 is made up of a plurality of channels and generates an additional magnetic field to correct the static magnetic field inhomogeneity, according to the current supplied from the shim power supply 114. The sequencer 104 controls the current flowing in the channels constituting the shim coil, upon adjusting the static magnetic field homogeneity.

[Imaging]

Operation from imaging to image reconstruction in the MRI apparatus 100 having the configuration as described above is the same as in a conventional MRI apparatus. In other words, when imaging is performed on a desired imaging area (imaging cross section) of a subject, the computer 120 delivers an instruction to the sequencer 104, so as to activate each part of the measurement unit according to programs provided in advance, and controls the operations of the units constituting the MRI apparatus 100. The sequencer 104 sends commands to the gradient power supply 105 and to the RF magnetic field generator 106, thereby allowing RF pulses to be applied to the subject 103 via the RF coil 107 along with applying gradient magnetic field pulses by the gradient coil 102, at a timing and with strength instructed from the computer 120. The gradient magnetic field is applied to provide echo signals with position information in a slice selective direction, in a phase encoding direction, and in a readout direction, and gradient pulses in three orthogonal axes are combined and used as appropriate.

The RF probe 108 receives nuclear magnetic resonance (hereinafter, referred to as NMR) signals (echo signals) generated by nuclear magnetization within tissues of the subject, and the receiver 109 performs detection (measurement) of the signals. The NMR signals are subjected to sampling for a predetermined sampling time, measured in the form of digital data, and then, placed in measurement space referred to as k-space. Measurement of the NMR signals is repeated until the k-space is filled with the signals. The signals thus measured are delivered to the computer 120. The computer 120 (image computing unit 10) performs inverse Fourier transform processing on the signals filled in the k-space, thereby reconstructing an image. The storage unit 112 stores the image thus generated, and if necessary, the storage unit also stores the signals after the detection, imaging conditions, and others.

Among the aforementioned programs executed by the computer 120, programs particularly describing application timing and strength of the RF magnetic field and the gradient magnetic field, and timing for receiving signals, are referred to as pulse sequences. Imaging is performed according the pulse sequence and imaging parameters necessary for controlling the pulse sequence. Control of the timing and strength of the RF magnetic field and the gradient magnetic field provided in the pulse sequence, allows imaging of any imaging cross section of the subject. The pulse sequence is created in advance and held in the storage unit 112. The imaging parameters are entered by the user via the input unit 116.

There are known various pulse sequences depending on the purpose. For example, a gradient echo (GrE) type fast imaging changes a phase encoding gradient magnetic field sequentially every repetition time (hereinafter, referred to as TR) of the pulse sequence, and measures NMR signals the number of which is required to obtain one tomographic image, or a three-dimensional image made up of a plurality of tomographic images. The imaging parameters may include, the repetition time TR, echo time TE, flip angle FA for determining RF pulse strength, and phase increment θ of RF pulses being applied. The settings of these parameters can be configured depending on an image to be taken.

The user configures the settings of the pulse sequence or the imaging parameters, depending on a physical property value to be emphasized in imaging, and the NMR signals obtained under thus provided imaging conditions are prone to strongly reflect the influence from the physical property value. Then, these signals are reconstructed as an image. Therefore, it is possible to obtain various weighted images with different degrees of emphasis on the physical property values, for example, T1 weighted image, T2 weighted image, a magnetic susceptibility weighted image, a diffusion weighted image, and other images (processing in the image reconstruction unit 121). Imaging of the weighted image is repeated more than once, with changing the imaging parameters, and obtained signals are processed. This allows calculation of a plurality of physical property values in the subject tissue at each pixel position of the image (processing in the physical property value calculator 122).

The physical property values may include, for example, T1 (longitudinal relaxation time), T2 (transverse relaxation time), T2* (apparent transverse relaxation time affected by static magnetic field inhomogeneity), PD (proton density), magnetic susceptibility, diffusion coefficient, and others. With those values, a quantitative image having the physical property value as a pixel value can be generated. That is, for example, T1 image having T1 as the pixel value, T2 image having T2 as the pixel value, and other similar images, can be generated. In addition, on the basis of the pixel values of the weighted image or the quantitative image, a new quantitative image (segmentation image) may also be obtained, having as the pixel value, the percentage of gray matter, white matter, and cerebrospinal fluid, with respect to typical ranges of the pixel values of living-body tissue such as the gray-white matter and white matter. A method for calculating the physical property value and imaging conditions required for the calculation are publicly known and specific descriptions thereof will not be provided here.

The image computing unit 10 may also perform processing such as standardization and statistics calculation, on the aforementioned images and physical property values, so as to use those images and physical property values for supporting image diagnosis and other purposes.

Specifically, the standardization unit 123 performs anatomical standardization, so that the weighted images or the quantitative images obtained by the measurement unit 110 can be compared in a coordinate system commonly used among test subjects. A publicly known method may be employed for the anatomical standardization. For example, there is a method where a brain segmentation image of the test subject and a standard-type brain segmentation image are used to calculate displacement vectors at points on the segmentation image of the subject. Then, thus calculated displacement vectors are used to perform non-rigid transformation.

According to the anatomical standardization, for example, a gray matter segmentation image in a standard brain coordinate system, can be obtained from the gray matter segmentation image of the subject. In this situation, transforming is performed in a manner that keeps a total sum of the pixel values the same between before and after the transformation, whereby a gray-matter density image is obtained with the pixel value representing a gray matter volume per pixel. Similarly, a white-matter density image and a cerebrospinal-fluid density image may also be obtained.

In addition, by using the displacement vectors being calculated, another weighted image or another quantitative image captured at an identical position can be transformed into an image in the standard brains coordinate system. Then, various weighted images or various quantitative images transformed into the images in the standard brain coordinate system can be obtained.

The statistic calculator 124 uses the captured image and the anatomically standardized image, so as to calculate statistics of brightness values and quantitative values in a partial area of the subject. For example, the coordinates of each of brain areas such as putamen and hippocampus defined in advance in the standard brain coordinate system are used, together with the images anatomically standardized, so as to calculate an average brightness value and an average quantitative value within each of the brain areas. There is variability among the pixel values, due to errors in the anatomical standardization and measurement noise, but taking the average of the values within each brain area allows obtainment of measured values with less variability. Not only the average value, but also other statistics may be calculated similarly, such as a total, a median value, a maximum value, a minimum value, and an interquartile range. The statistics thus calculated may be stored, for example, in the storage unit 112, and they may also be used for the purpose in addition to the image diagnosis support.

[Image Diagnosis Support Function]

The image diagnosis support unit 20 in the MRI apparatus, or the image diagnosis support device 200 that is activated upon receipt of measured data from the MRI apparatus, calculates information serving as an index for diagnosis, by using the weighted image, the quantitative value, the quantitative image, the statistics, and others (collectively referred to as "measured values") that are obtained according to the imaging procedures as described above. There will now be described a specific processing of the image diagnosis support unit 20. An overview of the processing corresponds to the flowchart as shown in FIG. 2, and thus the processing will be described with reference to FIG. 2, again.

In the present embodiment, by way of example, there will be described a case that statistics of the physical property values on a body part (region) basis are used, regarding a plurality of regions within brain, including hippocampus, putamen, orbitofrontal cortex, and others, so as to present diagnostic support information of brain disease. Regions and measured values to be used are not limited to those examples.

First, for the image diagnosis support, the measured-value receiving unit 210 receives from a user via the input unit 116, designation of information related to required diagnosis, and reads necessary measured values from those stored in the storage unit 112 (FIG. 1: storage unit 40) (S201).

Upon receipt of given various types of measured values at given multiple positions within a living body, the group generator 220 generates groups depending on the positions or the types of thus received measured values (S202). Next, the intermediate index calculator 230 calculates an intermediate index on a per-group basis, by using the measured values included in each group (S203). Finally, the comprehensive index calculator 240 calculates a comprehensive index from values of the intermediate index calculated on a per-group basis, and outputs the comprehensive index (S204, S205).

Hereinafter, details of each of the steps will be described.

[Step S201: Receive Measured Values]

Figure 5:
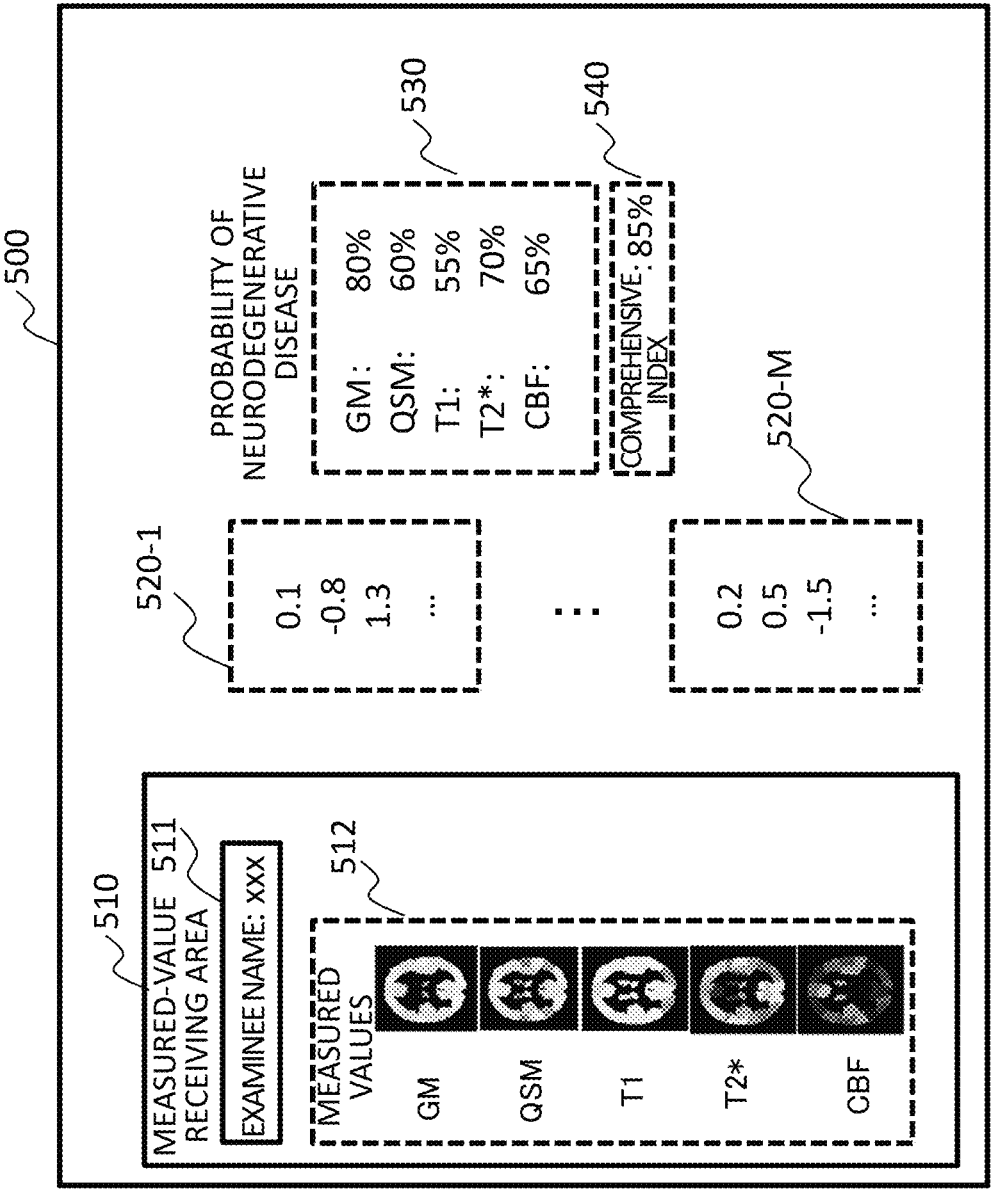
FIG. 5 illustrates one example of a user interface screen according to the first embodiment.

As shown in FIG. 5, first, the measured-value receiving unit 210 displays on the display unit 111, a screen (GUI) 500 for each element of the image diagnosis support unit 20 to perform I/O processing, along with providing a display area 510 for receiving an instruction from the user via the input unit 116 such as a mouse and a touch panel.

Next, the measured-value receiving unit 210 receives given various types of measured values at given multiple positions within a living body. For example, the measured-value receiving unit 210 receives as measured values, statistics for each region, such as gray-matter volume, average magnetic susceptibility (QSM), T1, T2*, and cerebral blood flow (CBF), in a plurality of brain regions (e.g., hippocampus, putamen, orbitofrontal cortex, and others). Specifically, a specific-data entry area 511 displayed on the measured-value receiving area 510 receives user's operation such as entry of the subject name and measured values being specified. Then, in response to thus received entries, measured values stored in the storage unit 112 are read out, thereby receiving the measured values. Thus received measured values may be displayed in a display area 512 for the entered measured values, facilitating the user to ascertain the measured values. In this example, there is described an example where the measured values are received in association with a region (statistics of each brain region such as putamen and hippocampus). However, the region and the measured value may be received separately. For example, according to a manual procedure or an automatic procedure using a publicly known segmentation method, a central region and a boundary region of tumor within an image are provided, and pixel values within the regions and statistics of the pixel values within the regions may be received as the measured values.

[Step S202: Generate Group]

Figure 6:
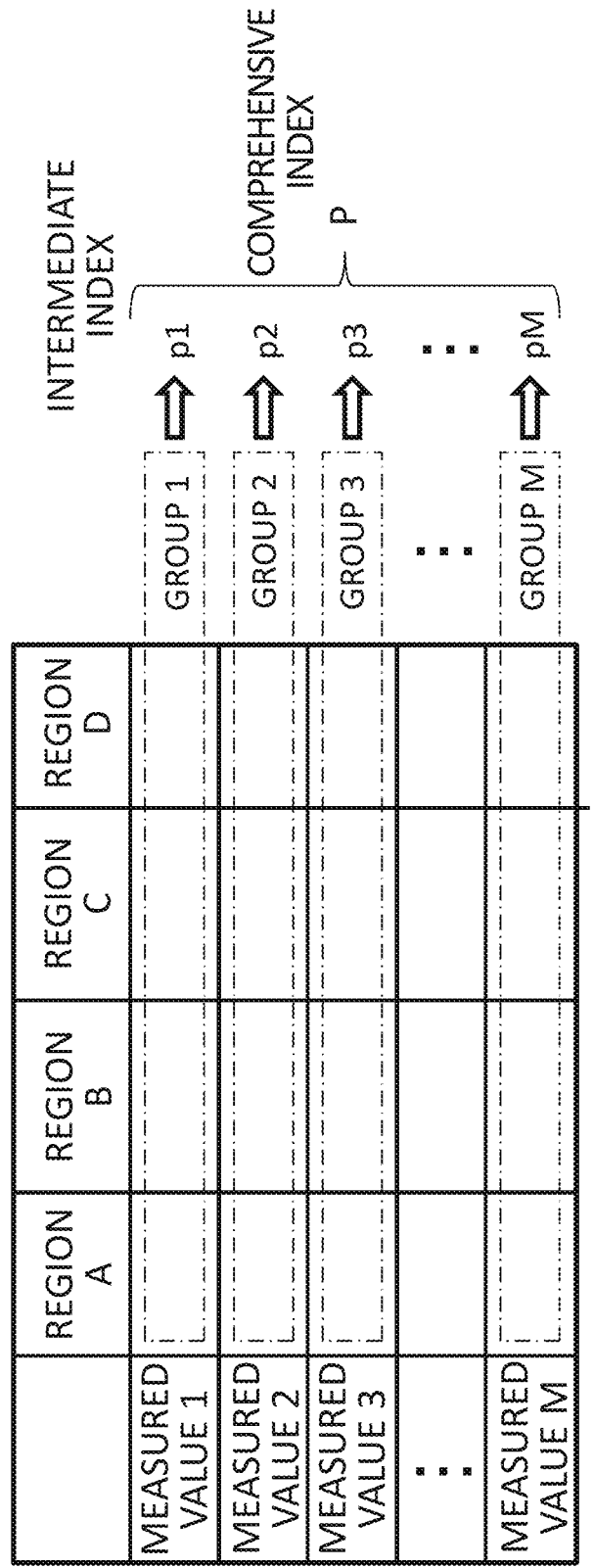
FIG. 6 illustrates one example of groups generated by a group generator according to the first embodiment.

The group generator 220 divides the multiple measured values received by the measured-value receiving unit 210, into groups depending on regions or types. As shown in FIG. 6, for example, the measured values received by the measured-value receiving unit 210 may be divided into groups on a measured-value type basis (e.g., gray-matter volume (GM), magnetic susceptibility, T1, T2, cerebral blood flow, and others). In this case, when there are M types of measured values, M groups are generated, and the number of the measured values included in each group corresponds to the number of regions where the measurement was performed. These measured values thus divided into groups are preserved in the form of vectors, in the storage unit of the computer 120, the measured values being sorted in a predetermined order (e.g., in the order of region name). In addition, in order to facilitate the user to ascertain the processing, the measured value vectors in M groups may be displayed numerically in the display areas 520-1 to 520-M.

[S203: Calculate Intermediate Index]

Next, the intermediate index calculator 230 calculates an intermediate index from the measured values included in the group, on a per-group basis generated by the group generator 220. In this example here, the probability of a certain disease is calculated as the intermediate index. For example, according to Equation 1, the vector xm of the measured values included in the m-th group is transformed into the index (probability) pm.

[Equation 1]

$$p_m = f(w_m \cdot x_m + b_m) \quad (1)$$

where wm is a coefficient vector for transforming xm, and bm is a constant for the transformation. In addition, f is logistic sigmoid function represented by Equation 2:

[Equation 2]

$$f(y) = \frac{1}{1 + \exp(-a_m y)} \quad (2)$$

In Equation 2, am is a constant. The coefficient vector wm and the constant bm in Equation 1, and the constant am in Equation 2 can be determined according to publicly known machine learning methods, such as logistic regression and support vector machine. In those methods, there is used learning data obtained in advance by dividing the measured values into groups in the same manner as described above, after similar measurement on another subject, i.e., a healthy person and a patient having a certain disease, who is different from the test subject.

Values of wm, bm, and am thus determined are stored in the storage unit 112, for example, and the intermediate index calculator 220 reads any of those values in calculating the index pm according to Equations 1 and 2. Alternatively, after receipt of the measured values by the measured-value receiving unit 210, the learning data stored in the storage unit 40 is read out, and then according to machine learning, those coefficients may be calculated. The index pm thus obtained represents the probability of a certain disease (e.g., neurodegenerative disease, cerebral infarction, and so on) estimated from the measured value xm of the m-th group. Transformation performed as to each of the groups generated by the group generator 220 allows calculation of one intermediate index (in the present example, the probability pm of disease) from each group.

Thus calculated intermediate index may be displayed in the intermediate index display area 530 in the display screen as shown in FIG. 5, for example, together with the names indicating the groups (e.g., gray matter (GM), magnetic susceptibility (QSM), T1, T2, and cerebral blood flow (CBF)).

[S204: Calculate Comprehensive Index]

The comprehensive index calculator 240 uses as an input, the intermediate index calculated by the intermediate index calculator 230, and calculates a comprehensive index. For example, the comprehensive index uses as the input, a vector given by aligned numerical values of the intermediate index calculated by the intermediate index calculator, so as to calculate the probability of a certain disease, as the comprehensive index according to Equation 3:

[Equation 3]

$$p = \frac{\prod_{m=1}^{M} p_m}{\prod_{m=1}^{M} p_m + \prod_{m=1}^{M} (1 - p_m)} \quad (3)$$

Then, the comprehensive index is obtained to be used for diagnosis. For example, the comprehensive index may be displayed in the form of number in the comprehensive index display area 540 (FIG. 5) (S205).

As described so far, according to the present embodiment, information to be used for the image diagnosis support is divided into groups, and the intermediate index is calculated by machine learning for the determination on a per-group basis. Therefore, in comparison to the case where all the measured values are used to perform determination at once, the number of vector dimensions becomes less, and determination with high accuracy is possible, even when learning is performed with a smaller number of learning data. Further, according to the present embodiment, not only the comprehensive index used finally in diagnosis, but also the intermediate index on a per-group basis can be displayed. Thus, this facilitates the user to ascertain the basis for the calculation of the final comprehensive index and to perform diagnosis without difficulty.

Further according to the present embodiment, since the medical image acquisition apparatus itself has the function of image diagnosis support, this allows provision of information usable for a doctor who is the user of the apparatus, and also promotes efficient imaging used for the diagnosis.

Modification 1 of First Embodiment

In the first embodiment, the intermediate index calculated by the intermediate index calculator 230, and the comprehensive index calculated by the comprehensive index calculator 240 indicate the probability of a certain disease. However, there may be considered various types of indexes besides the probability. For example, the index may be a value indicating a stage of a certain disease, in accordance with the progress of neurodegenerative disease such as dementia (major neurocognitive disorder). For example, the value is 0 for the normal stage, nearly 1 for the mild stage, and nearly 2 for the severe stage.

In order to represent the progress of the disease, for example, the intermediate index calculator 230 uses the linear function gm given by Equation 4 to calculate the intermediate index sm from the measured values xm on a per-group basis:

[Equation 4]

$$s_m = g_m(x_m) = w'_m \cdot x_m + b'_m \quad (4)$$

where w'm is a coefficient vector, and b'm is a constant.

In addition, the comprehensive index calculator 240 calculates the comprehensive index S from values of the intermediate index sm on a per-group basis, by using the linear function g given by Equation 5 as the following:

[Equation 5]

$$S = g(s_1, \ldots, s_m) = w' \cdot s + b' \quad (5)$$

where s is a vector having s1 to sm being aligned, w' is a coefficient vector, and b' is a constant.

In Equations 4 and 5, w'm, b'm, w' and b' may be determined, for example, according to the least-square method, by using learning data where the intermediate index sm and the comprehensive index S have been defined (e.g., manually set by a doctor), being correct answers in the past measurement. For example, according to a support vector machine, a plane that separates between a disease group and a normal group is determined, thereby calculating a degree of progression (stage) based on a distance from the plane. Various types of functions may also be used as the functions gm and g, besides the linear function. For example, there may be used a function such as a polynomial expression, a logistic sigmoid function, an exponential function, a trigonometric function, a step function, a soft-max function, Rectified Linear (ReLU) function, and a neural network combining those functions as described above. Parameters for these functions may also be determined by the least-square method, or various publicly known machine learning methods.

Accuracy may be improved more, by using an adequate function depending on the type (the probability, the degree of progress, or others) of the outputted intermediate index and comprehensive index, the number of training data, and the type of the measured value and a range of the value. This configuration facilitates the user, i.e., the doctor who performs diagnosis, to ascertain the stage of the disease. When the measured value is set with designation of a region (a certain area and an area other than the certain area), the type and the stage of disease occurring locally can be determined.

In addition, values of the intermediate index and the comprehensive index may represent a type of disease. For example, it is possible to output a value in association with the type of disease, for example, the value is zero for the case of a healthy person, the value is 1 for the case of cerebral infarction, and the value is 2 for the case of cerebral hemorrhage. For example, a publicly known machine learning method such as the neural network and the support vector machine may be used as a function to output the value indicating the type of disease, out of such various types of diseases as described above.

Furthermore, the intermediate index and the comprehensive index may be configured in a manner that represents how much the value falls outside the range of a standard value of a healthy person, that is, representing a degree of abnormality. For example, average μm and variance-covariance matrix Em of xm of the healthy person are used instead of the function gm in Equation 4, so as to calculate Mahalanobis distance as the intermediate index sm according to Equation 6 as the following:

[Equation 6]

$$s_m = g_m(x_m) = \sqrt{(x_m - \mu_m)^T \Sigma_m^{-1}(x_m - \mu_m)} \quad (6)$$

The Mahalanobis distance becomes zero when the measured value agrees with the average value, and becomes a larger numeric value, with departing from the average, indicating the degree of abnormality. It is also possible to calculate the Mahalanobis distance of the intermediate index sm, instead of the function g in Equation 5. Determination of the abnormality, without limited to a specific disease, allows reduction of the number of images and regions to be checked by a doctor, thereby decreasing the burden on the doctor.

It is alternatively possible to configure such that a value from 0 to 1 represents the probability of a certain disease and abnormality, instead of a value representing the certain disease or the degree of abnormality itself. This may produce an advantage that allows diagnosis or decision of treatment, in response to the probability.

Values of the intermediate index and the comprehensive index may have the same characteristic (e.g., both represent the probability of a certain disease) for user's ease of understanding, but they are not necessarily the same. Furthermore, the intermediate index calculator 230 may display another value calculated from the intermediate index, instead of the intermediate index itself.

Modification 2 of First Embodiment

In the first embodiment, the intermediate index calculator 230 is described taking an example that one intermediate index is calculated on a per-group basis. It is further possible to configure such that multiple intermediate indexes are calculated by using a plurality of calculating methods group by group. For example, both the degree of abnormality and the probability of a certain disease may be calculated on a per-group basis. This configuration gives an advantage not only the user can check whether or not there is a disease, but also the user can simultaneously ascertain there is another abnormality. It is further possible to calculate the probabilities of a plurality of diseases as the intermediate indexes, for example, the probability of cerebral infarction and the probability of neurodegenerative disease. This produces an advantage that a plurality of diseases can be diagnosed simultaneously. Similarly, the comprehensive index may also be configured such that a plurality of values is calculated as the index.

Modification 3 of First Embodiment

In the first embodiment, there has been described an example that the measured-value receiving unit 210 receives as the measured values, the statistics of a plurality of regions within the subject. In addition, various values may be used as the measured values that are received by the measured-value receiving unit 210, including brightness values and quantitative values of various medical images, or statistics calculated therefrom.

In the MRI apparatus, in particular, various types of images at an identical position can be obtained depending on an imaging method. Therefore, usage of brightness values of various weighted images or quantitative values of quantitative images may produce an advantage that accuracy in disease determination can be enhanced. Specifically, it is preferable to use the values measured in the MRI apparatus, including quantitative values such as proton density, longitudinal relaxation time, longitudinal reflexivity, transverse relaxation time, transverse reflexivity, diffusion coefficient, a flow rate, blood flow volume, magnetic susceptibility, modulus of elasticity, concentration of contrast agent, a ratio of gray matter, a ratio of white matter, and a ratio of cerebrospinal fluid, or statistics calculated from those quantitative values. Those quantitative values or the statistics are independent of the imaging method, unlike the brightness values of the weighted image, and thus there is less variability. Accordingly, there is an expectation for higher accuracy in disease determination.

Modification 4 of First Embodiment

Figure 7:
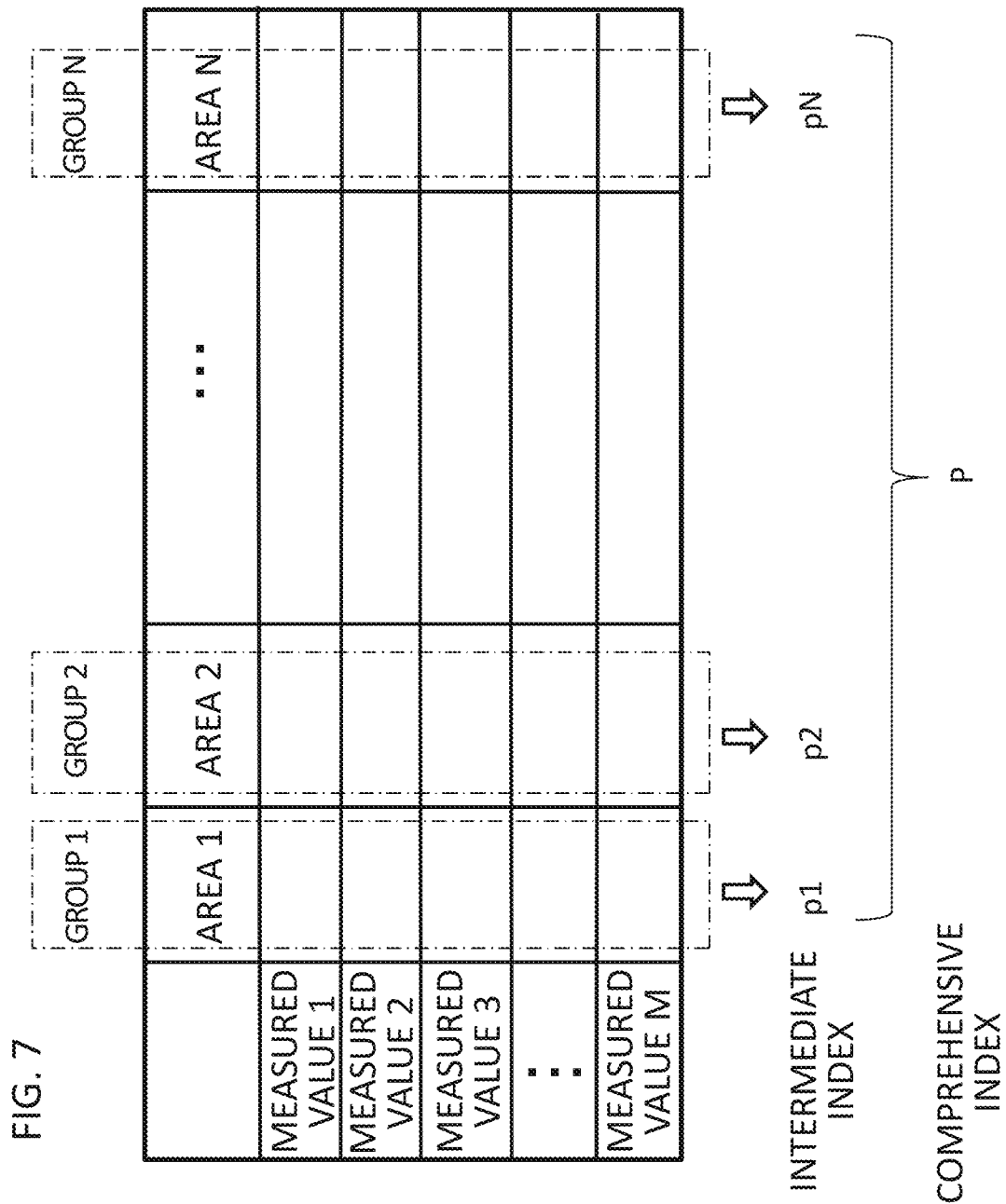
FIG. 7 illustrates another example (Modification 4) of the groups generated by the group generator according to the first embodiment.
Figure 8:
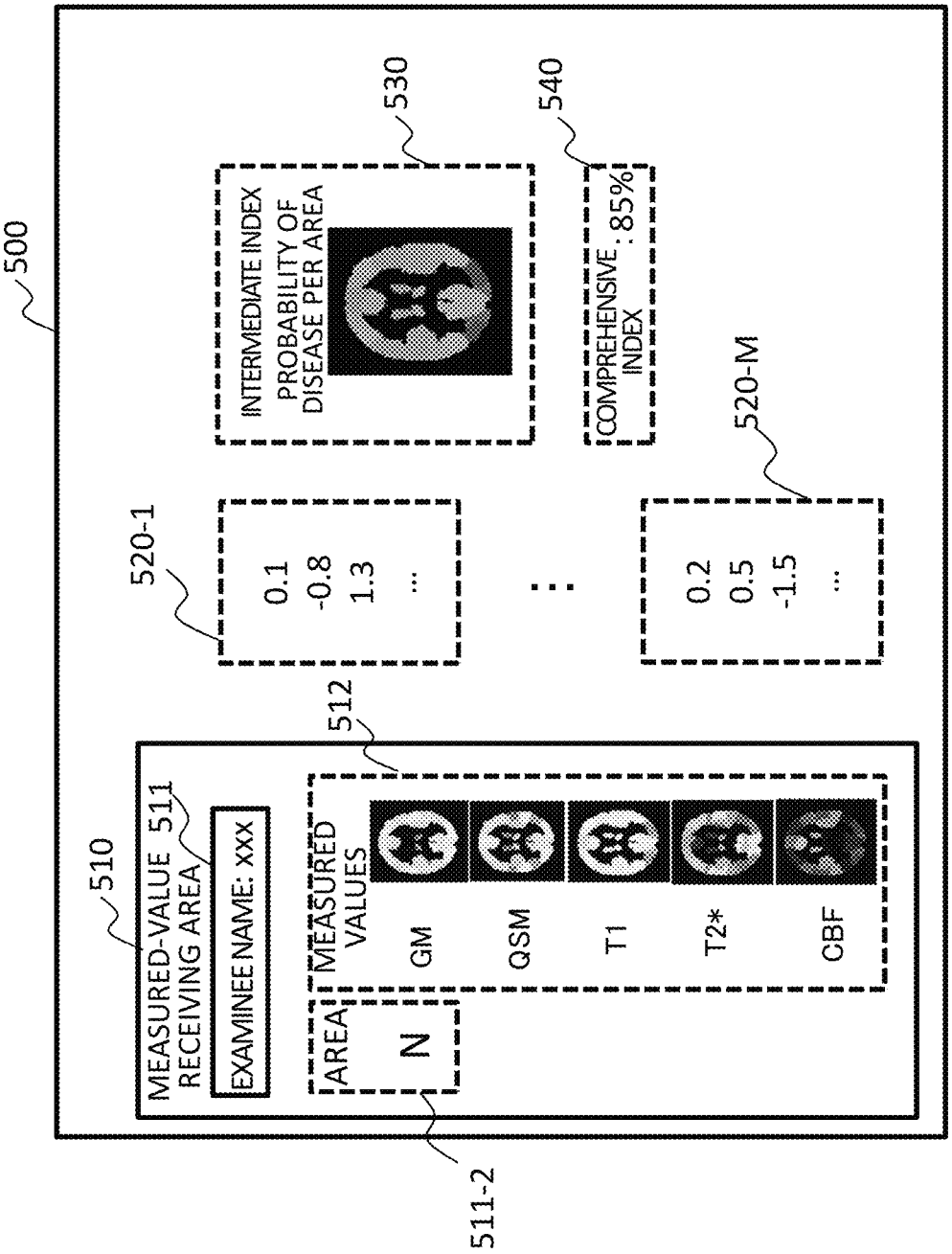
FIG. 8 illustrates one example of the user interface screen of Modification 4 according to the first embodiment.

In the first embodiment, groups are generated on a measured-value type basis (FIG. 6). As shown in FIG. 7, The groups may also be generated on a position (area) basis where the measured value is obtained. In this case, as shown in FIG. 8, the intermediate index may be displayed in the form of image where the values of the intermediate index are displayed using the brightness values or color coded, on a per-area basis. Setting of any area is possible, and similar to the first embodiment, the areas may correspond to a plurality of regions within the brain. It is further possible that an image is partitioned into approximately several tens of, or a hundred and several tens of areas. Alternatively, setting of a specific one or more areas and the other areas is possible. On the user interface screen (FIG. 8) for the image diagnosis support, a specified-data entry area 511 may be provided including the area 511-2 for entering the position of the area or the number of partitions.

According to the present modification, not the intermediate index on a measured-value type basis, but the intermediate index on a per-area basis is calculated, and thus there is an advantage that displaying the intermediate index facilitates a doctor to ascertain which part is abnormal and a type or the progression of the disease occurring locally.

In the first embodiment, all the measured values are divided into groups, and an index is calculated by using all the measured values within the group, but it is not necessary to use all the measured values for the group generation. For example, it is also possible to generate a group including the measured values of some regions in association with a certain disease, for example, a group indicating gray-matter volume of some regions such as hippocampus and parahippocampal gyrus included in the limbic system, and a group indicating cerebral blood flow of some regions such as posterior cingulate cortex and precuneus included in the occipital lobe. Using the regions to which already-known medical findings are applicable may produce an advantage that enhances accuracy.

There have been described so far, the first embodiment and its modifications. Those modifications as described above may be combined as appropriate as far as there is no technical contradiction.

Second Embodiment

In the present embodiment, the MRI apparatus has basically the same configuration as the MRI apparatus of the first embodiment (FIG. 4: image diagnosis support unit 20). Unlike the first embodiment, however, the intermediate index is calculated in multiple stages in the present embodiment. This configuration further enhances the accuracy in determining disease or others. There will now be described an example that the intermediate index is calculated in two stages.

Figure 9:
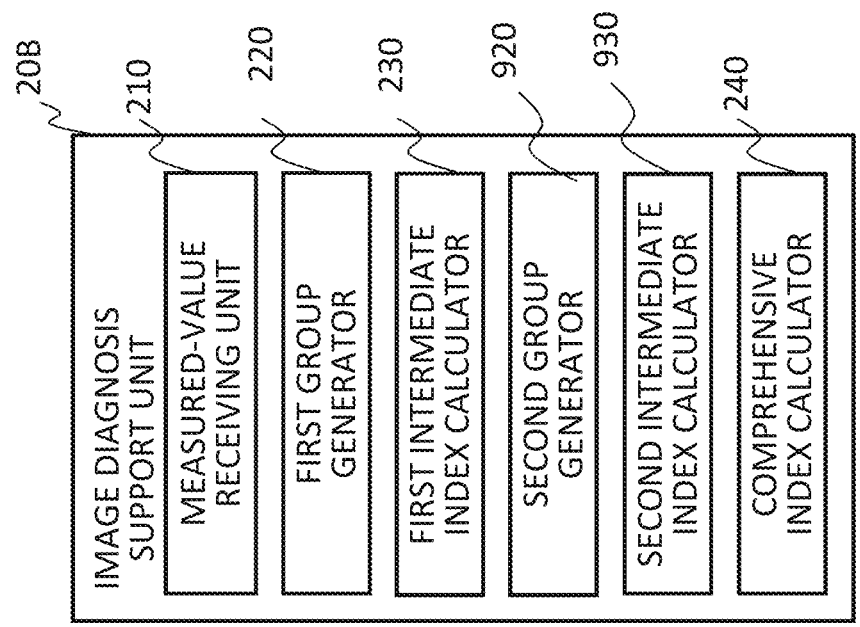
FIG. 9 is a functional block diagram of the computer (an image diagnosis support unit) according to a second embodiment.

As shown in FIG. 9, the image diagnosis support unit 20B of the present embodiment is provided with a second group generator 920 in addition to the first group generator 220 that has the same function as the group generator 220 of the first embodiment, and a second intermediate index calculator 930 in addition to the first intermediate index calculator 230 having the same function as the intermediate index calculator of the first embodiment.

Figure 10:
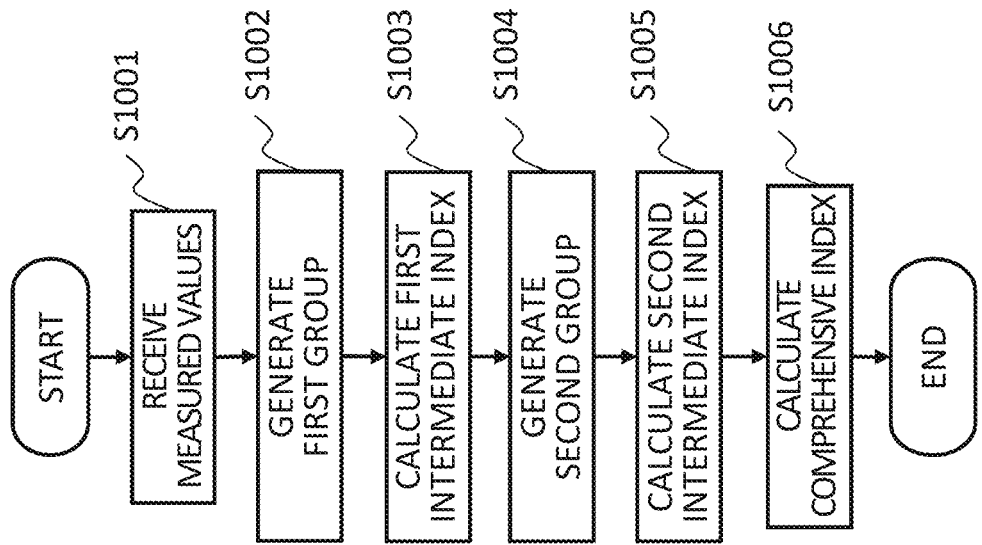
FIG. 10 is a flowchart showing an operation of the image diagnosis support unit according to the second embodiment.

Processing of the present embodiment will be described with reference to the flowchart as shown in FIG. 10.

There will be described an overview of the processing. First, the measured-value receiving unit 210 receives designation of a body part (region) and measured values as to a certain subject, and reads measured values of thus received designation from the storage unit 112 (S1001). Then, the first group generator 220 divides the measured values into a plurality of groups (a first group) (S1002), and the first intermediate index calculator 230 calculates the intermediate index (the first intermediate index) as to each of groups in the first group (S1003). After the first intermediate index is calculated, the second group generator 920 further divides values of the intermediate index of the respective groups into groups on a position basis, or on a measured-value type basis, to generate second groups (S1004). Then, the second intermediate index calculator 822 uses the values of the first intermediate index included in the second group generated by the second group generator 920, so as to calculate a second intermediate index (S1005). Finally, the comprehensive index calculator 240 uses values of the second intermediate index to calculate and output a comprehensive index (S1006).

There will now be described each of the steps in detail, based on a specific example.
[S1001: Read Measured Values]

Figure 11:
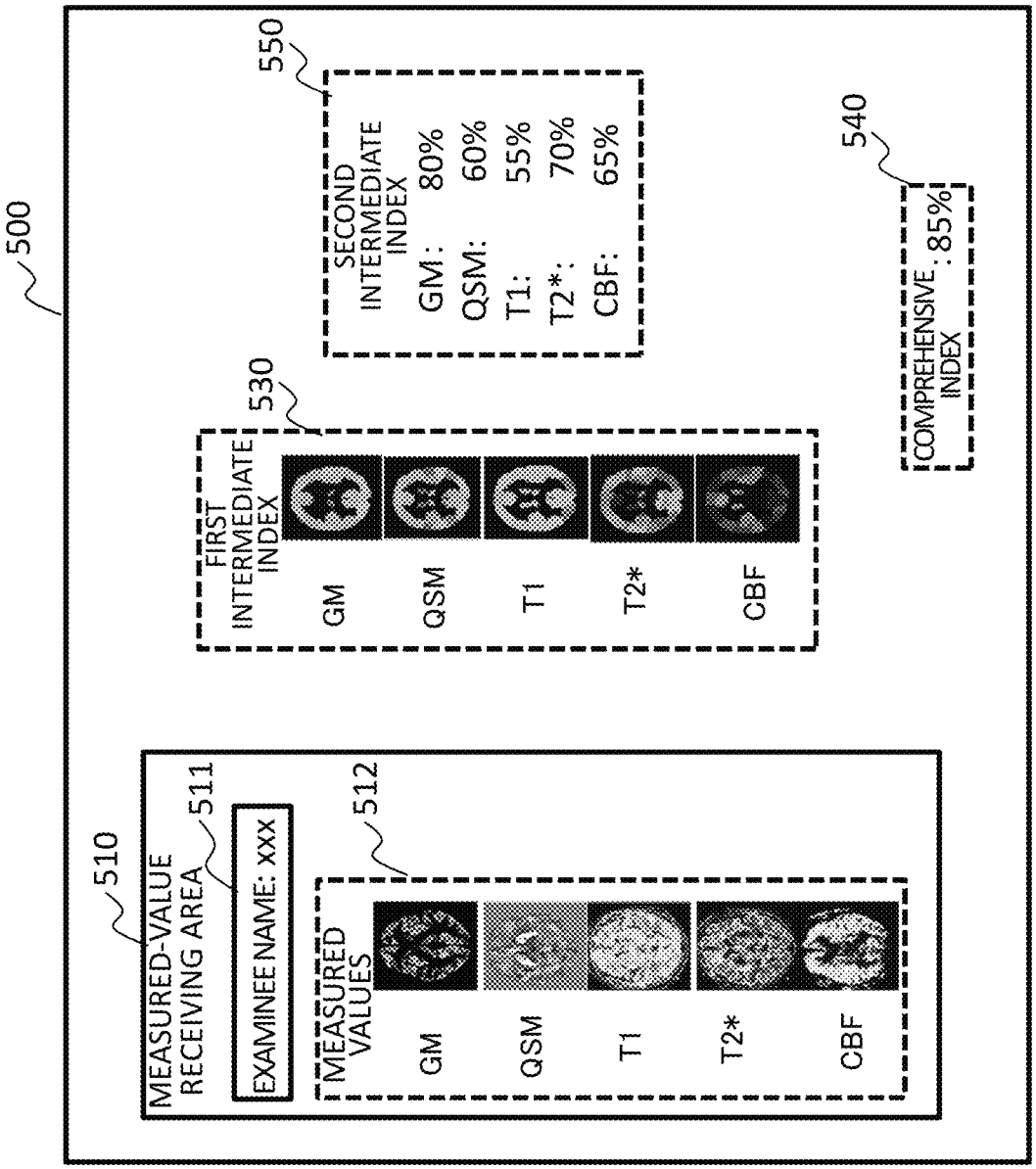
FIG. 11 illustrates one example of the user interface screen according to the second embodiment.

Similar to the first embodiment, the measured-value receiving unit 210 displays the screen 500 as shown in FIG. 11 on the display unit 111. Then, via the specified-data entry area 511, user's operation is accepted, such as entry of the name of an examinee and measured values.

In the first embodiment, statistics of quantitative values obtained from computation of an image are entered as the measured values. In the present embodiment, there will be described an example that the measured-value receiving unit 210 receives a quantitative image itself. By way of example, the measured-value receiving unit 210 accepts as the quantitative image, a gray-matter probability image, a magnetic susceptibility image, T1 image, T2* image, and a cerebral blood flow image, having been transformed to the standard brain coordinate system.
[S1002: Generate First Group]

One quantitative image of one region (body part) received by the measured-value receiving unit 210 includes as the measured values, quantitative values corresponding to the number of pixels. As shown in FIG. 12, the first group generator 220 generates measured-value groups, both on a quantitative-value basis and on a region basis. In other words, measured values of each type (gray-matter probability, magnetic susceptibility, T1, T2*, cerebral blood flow, and others), in each region of brain (e.g., the frontal lobe, the limbic system, basal ganglia, and others), corresponding to the pixels included in each region, are collectively allocated to one group. When there are M types of measured values and N regions, M×N groups are generated (in the example as shown in FIG. 12, 20 (=5×4) groups are generated. These groups are stored in the storage unit 112 in the form of vector having the pixel values aligned in a certain order.
[S1003: Calculate First Index]

Similar to the intermediate index calculator of the first embodiment, the first intermediate index calculator 230 calculates the intermediate index (the first intermediate index) from the measured values included in the group, as to each of the groups generated by the first group generator 220. A method for calculating the intermediate index is the same as the first embodiment, and a method suitable for the type of the index is employed for the calculation, the types of the index including, the probability of a certain disease, the presence or absence of abnormality, a progression of a specific disease, and so on. In the present embodiment, there are M×N groups, and thus M×N intermediate index values are calculated. As shown in FIG. 11, thus calculated intermediate index may be displayed in the intermediate index calculation area 530. Various display modes may be employed, such as a list of numerical values. A hue or brightness may be allocated to values of the index, and as shown in FIG. 11, images colored with the intermediate index values calculated for each region in the brain can be displayed. In the present embodiment, there are calculated [the number of the measured-value types]×[the number of regions or areas] intermediate index values, and thus displaying in the form of images is advantageous because this may facilitate visual understanding, better than just a list of numbers.

[S1004: Generate Second Group]

Next, the second group generator 920 of the present embodiment further divides the groups both on a measured-value basis and on a region basis, into groups either on a measured-value basis or on a region basis. In here, depending on the type of the measured value, as an example, second groups of the intermediate index are generated. When there are M types of image (measured values) being entered, the number of the second groups becomes M. Then, each group includes values of the intermediate index calculated on an image-type basis.

[S1005: Calculate Second Intermediate Index]

Next, the second intermediate index calculator 930 calculates the second intermediate index, as to each second group generated by the second group generator 920, by using the values of the first intermediate index included in the second group. The second intermediate index can be obtained by substituting the vector of the first intermediate index into the vector xm in Equation 1, which is used to calculate the intermediate index in the first embodiment. A method for determining the coefficient and the constant in Equation 1 is the same as the first embodiment, and they are determined by machine learning using as learning data, the data having been calculated through the same processing on the measured values obtained in a subject different from the subject being a target for the image diagnosis. Thus calculated values of the second intermediate index are displayed in the second intermediate index display area 550.

[S1006: Calculate Comprehensive Index]

The comprehensive index calculator 240 substitutes the second intermediate index into Equation 3 and calculates the comprehensive index. The comprehensive index is displayed in the comprehensive index display area 540. According to the present embodiment, even though the measured values (input) received by the receiving unit is data with a large number of dimensions after vectorization, such as the quantitative value for each pixel of an image, grouping is performed in multiple stages, and the intermediate index is calculated in each stage. Accordingly, even when there is a small number of learning data used for the machine learning, learning accuracy can be enhanced, and thus accuracy in determination is improved.

Modification of Second Embodiment

In the second embodiment, the first intermediate index is calculated both on an image-type basis and on a region basis, and the second intermediate index is calculated on an image-type basis. How to perform grouping in each of the first group generator and the second group generator may be changed variously, depending on how to make determination; determination on the basis of image type, or determination on the basis of region, or determination considering easiness in estimating lesion area.

Figure 13:
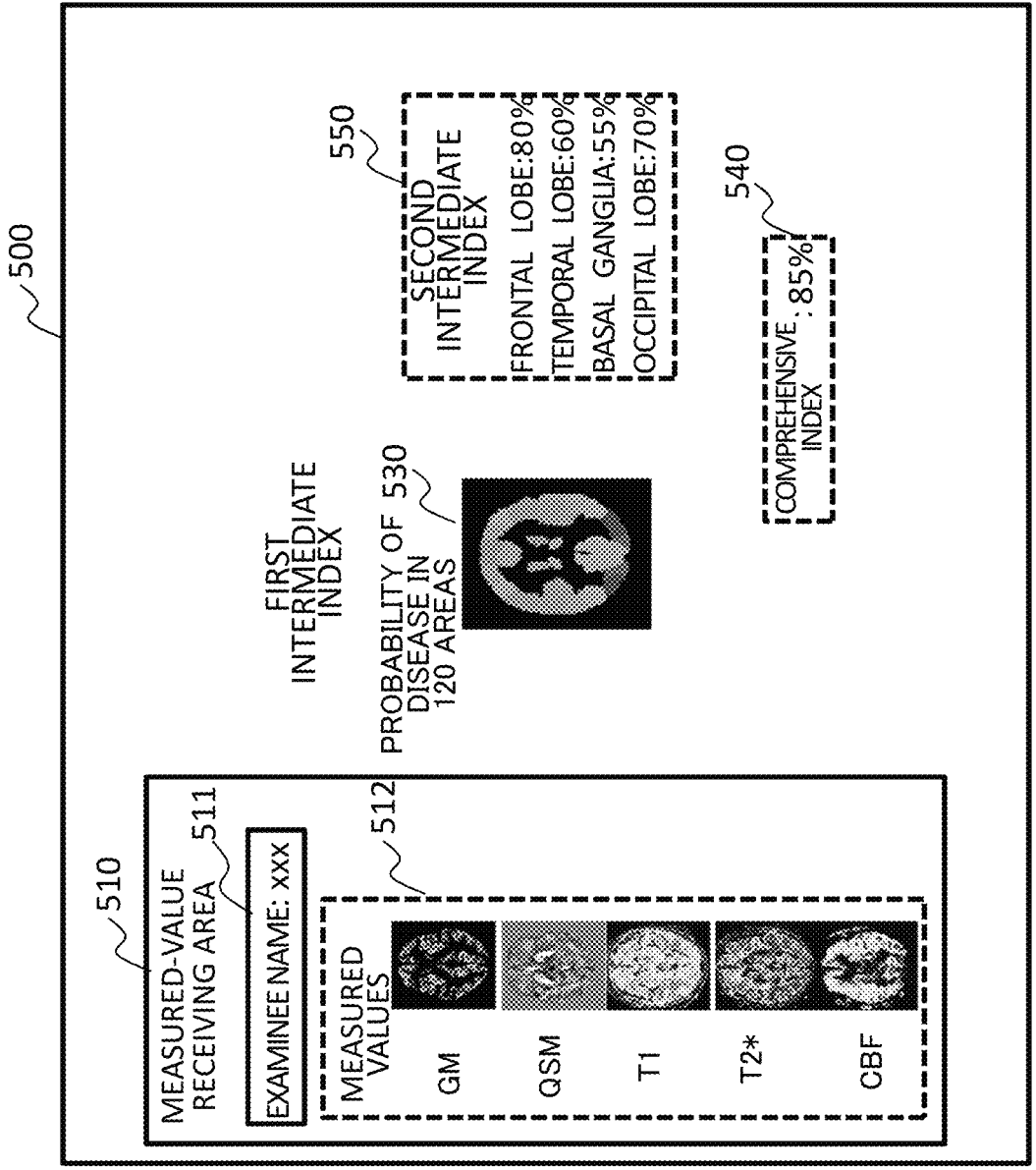
FIG. 13 illustrates a modification of the user interface screen according to the second embodiment.

For example, by using the first intermediate index calculated both on an image-type basis and on a region basis, the second intermediate index on a region basis may be calculated. It is alternatively possible to configure such that the first intermediate index may be calculated on a fine-region basis, the number of the fine regions is large, and the second intermediate index may be calculated on a large-region basis, the number of the large regions is small. In this case, for example, the first group generator 220 generates a large number of groups, by dividing the measured values into a large number of fine regions (e.g., 120 areas), such as hippocampus, orbitofrontal cortex, and posterior cingulate cortex. In the group of each area, there are included various types of measured values, and each measured value may be the statistics of the measured values within the region, for instance. The first intermediate index calculator 230 uses the measured values included in each group to calculate the first intermediate index, and displays values of the first intermediate index in the intermediate index display area 530. A display mode in this case may be a list of numerical values, or a table, but more preferably, as shown in FIG. 13, the index in each area may be displayed in an image representing the index values by color-coding or brightness.

The second group generator 920 divides the large number of fine regions grouped by the first group generator 220, into some groups (e.g., the frontal lobe, the occipital lobe, and others), that is, a small number of broad regions (e.g., four regions). The second intermediate index calculator 930 calculates the second intermediate index from the values of the first intermediate index included in the group, for each of the small number of broad regions generated by the second group generator 920. As shown in FIG. 13, values of the second intermediate index of the respective regions thus calculated are displayed in the second intermediate index display area 550. Finally, the comprehensive index calculator 240 substitutes the values of the second intermediate index into Equation 3 to calculate the comprehensive index, and displays the index in the comprehensive index display area 540.

The present modification is advantageous because this allows hierarchical understanding at a glance, in which part abnormality occurs.

There has been described so far, the modification of the second embodiment where a different method of group generation is employed. The modifications described in the first embodiment are similarly employed in the second embodiment, the modifications including, changing the type of measured values, using different types of index between the intermediate index and the comprehensive index or using a plurality of intermediate indexes and comprehensive indexes, and variation of the index type, for instance. The method for calculating the indexes and a machine learning algorithm (learning data to be used) may be modified appropriately, thereby allowing variation of a combination of the measured values and the indexes, the types of the index, and others.

There has been described so far, the MRI apparatus equipped with the image diagnosis support function. However, the MRI apparatus is not the only example of the medical image acquisition apparatus, but the present invention may be applicable to any publicly known various medical image acquisition apparatuses. In the aforementioned embodiments, there has been described the case where one medical image acquisition apparatus uses the measured values acquired within the apparatus to perform the image diagnostic support. However, any measured value acquired in another modality may be used for the diagnosis support. For example, a CT image acquired by a CT apparatus and quantitative values such as a blood flow image and blood flow volume acquired by an ultrasonic diagnostic device may be captured, and thus captured information is also usable for the diagnostic support in a composite manner.

What is claimed is:

1. An image diagnosis support device comprising,
a processor;
a display coupled to the processor;
a memory coupled to the processor, the memory storing instructions that when executed by the processor configure the processor to:
receive various types of measured values at a plurality of positions within a diagnosis target of a living body,
divide the measured values into a plurality of groups depending on the position or the type of the measured value,
calculate a plurality of values of an intermediate index, where each value of the intermediate index is a diagnosis index of each of the plurality of the groups calculated from the measured values included in the group on a per-group basis, and
calculate a comprehensive index, as a diagnosis index of the diagnosis target, by merging from values of the intermediate index calculated on a per-group basis,
display a part or all of values of the calculated intermediate index in the form of numbers or in the form of images.

2. The image diagnosis support device according to claim 1,
wherein the measured value is any of the following: an original image, quantitative values calculated from the original image, a quantitative image having the quantitative values as pixel values, and statistics calculated from the original image or the quantitative image.

3. The image diagnosis support device according to claim 1,
wherein the intermediate index and the comprehensive index include any of the following: presence or absence of a disease or the probability of the disease, a degree of disease progression, and presence or absence of abnormality or the probability of the abnormality.

4. The image diagnosis support device according to claim 3,
wherein the intermediate index and the comprehensive index indicate an identical index.

5. The image diagnosis support device according to claim 3,
wherein the intermediate index and the comprehensive index indicate different indexes.

6. The image diagnosis support device according to claim 1,
wherein the processor is configured to calculate the intermediate index on the basis of learning data measured from a second living body different from the living body as to which the measured-value receiving unit receives the measured values.

7. The image diagnosis support device according to claim 6,
wherein the processor is configured to calculate the intermediate index by using a neural network comprising a function having a coefficient and a constant defined according to machine learning, or comprising a combination of more than one function having the coefficient and the constant defined according to the machine learning.

8. The image diagnosis support device according to claim 1,
wherein the processor is configured to: divide the measured values into a plurality of groups, and further divide the plurality of groups into a second plurality of groups,
calculate a first intermediate index on a per-group basis of the plurality of groups generated by the first group generator, by using the measured values included in the groups, and calculate a second intermediate index from the second plurality of groups generated by the second group generator, by using values of the first intermediate index, and
calculate a comprehensive index by using values of the second intermediate index.

9. The image diagnosis support device according to claim 8,
wherein the processor is configured to generate the plurality of groups, so that the measured values of the same type at the same position are put into one group, and the generate the second plurality of groups, by grouping the plurality of groups generated by the first group generator into one group, in such a manner that the groups having the measured values at the same position are put into one group, or the groups having the measured values of the same type are put into one group.

10. The image diagnosis support device according to claim 8,
wherein the processor is configured to generate groups by partitioning the measured values into a plurality of small areas, on the basis of the position, and
generate groups by merging and then partitioning the small areas into large areas.

11. A medical image acquisition apparatus, comprising
a gradient coil;
RF coil;
an RF magnetic field generator configured to drive the RF coil;
a receiver configured to detect echo signals;
a sequencer configured to send commands to the gradient power supply and to the RF magnetic field generator;
a processor;
a memory coupled to the processor, the memory storing instructions that when executed by the processor configure the processor to:
reconstruct the image of a subject by using the echo signals,
calculate various types of images at a plurality of positions within a diagnosis target of the subject, or statistics of the images, and
present an index related to a disease of the subject by using measured values,
divide the measured values into a plurality of groups depending on the position or the type of the measured value,
calculate a plurality of values of an intermediate index, where each value of the intermediate index is a diagnosis index of each of the plurality of the groups calculated from the measured values included in the group on a per-group basis, calculate a comprehensive index, as a diagnosis index of the diagnosis target, by merging from values of the intermediate index calculated on a per-group basis, and displaying, on a display, a part or all of values of the calculated intermediate index in the form of numbers or in the form of images.

12. The medical image acquisition apparatus, according to claim 11, wherein the measured values include a weighted image or a quantitative image, being obtained by performing computations on the nuclear magnetic resonance signals, or statistics of the weighted image or the quantitative image, being calculated from pixel values within a predetermined area.

13. The medical image acquisition apparatus, according to claim 12, wherein the measured values include any of proton density, longitudinal relaxation time, longitudinal reflexivity, transverse relaxation time, transverse reflexivity, diffusion coefficient, a flow rate, blood flow volume, magnetic susceptibility, modulus of elasticity, concentration of contrast agent, a ratio of gray matter, a ratio of white matter, and a ratio of cerebrospinal fluid, or statistics calculated from the measured values.

* * * * *